United States Patent
Yoo et al.

(10) Patent No.: US 10,644,186 B2
(45) Date of Patent: May 5, 2020

(54) BIO-INFORMATION DETECTING SENSOR

(71) Applicant: KOREA ADVANCED INSTITUTE OF SCIENCE AND TECHNOLOGY, Daejeon (KR)

(72) Inventors: Seunghyup Yoo, Daejeon (KR); Hyeonwoo Lee, Goyang-si (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 0 days.

(21) Appl. No.: 16/235,055

(22) Filed: Dec. 28, 2018

(65) Prior Publication Data

US 2019/0313954 A1    Oct. 17, 2019

(30) Foreign Application Priority Data

Mar. 30, 2018    (KR) .................... 10-2018-0037002

(51) Int. Cl.
*H01L 31/12*    (2006.01)
*A61B 5/1455*    (2006.01)
(Continued)

(52) U.S. Cl.
CPC ............. *H01L 31/125* (2013.01); *A61B 1/05* (2013.01); *A61B 1/06* (2013.01); *A61B 1/0607* (2013.01); *A61B 1/0684* (2013.01); *A61B 5/0059* (2013.01); *A61B 5/0261* (2013.01); *A61B 5/02444* (2013.01); *A61B 5/1455* (2013.01); *A61B 5/14552* (2013.01); *H01L 23/5387* (2013.01); *H01L 25/18* (2013.01);
(Continued)

(58) Field of Classification Search
CPC ........... A61B 1/05; A61B 1/06; A61B 1/0607; A61B 1/0684; A61B 5/0059; A61B 5/02444; A61B 5/026; A61B 5/0261; A61B 5/1455; A61B 5/14552; H01L 31/12; H01L 31/125; H01L 31/14; H01L 31/141; H01L 31/143; H01L 31/145; H01L 31/153; H01L 31/16; H01L 31/173
See application file for complete search history.

(56) References Cited

U.S. PATENT DOCUMENTS

| | | | |
|---|---|---|---|
| 2016/0238439 A1* | 8/2016 | Chu | ....................... H01L 25/167 |
| 2017/0042484 A1* | 2/2017 | Chong | ................. A61B 5/1455 |

(Continued)

FOREIGN PATENT DOCUMENTS

| | | | |
|---|---|---|---|
| JP | 2010-167089 A | 8/2010 | |
| JP | 2013-009710 A | 1/2013 | |

(Continued)

OTHER PUBLICATIONS

Lee et al., "Toward all-day wearable health monitoring: An ultralow-power, reflective organic pulse oximetry sensing patch" Science Advances, Supplementary Material, Nov. 9, 2018.
(Continued)

*Primary Examiner* — Eduardo A Rodela
(74) *Attorney, Agent, or Firm* — Maschoff Brennan

(57) ABSTRACT

A bio-information detecting sensor according to an embodiment of the present invention includes a flexible substrate, light emitting parts disposed on the flexible substrate, and a light receiving part disposed on the flexible substrate and having a donut shape surrounding the light emitting parts.

11 Claims, 7 Drawing Sheets

(51) Int. Cl.
*H01L 25/18* (2006.01)
*H01L 23/538* (2006.01)
*H01L 51/00* (2006.01)
*H01L 51/44* (2006.01)
*H01L 51/52* (2006.01)
*H01L 31/14* (2006.01)
*H01L 31/173* (2006.01)
*H01L 31/153* (2006.01)
*H01L 31/16* (2006.01)
*A61B 5/026* (2006.01)
*A61B 5/00* (2006.01)
*A61B 1/05* (2006.01)
*A61B 1/06* (2006.01)
*A61B 5/024* (2006.01)

(52) U.S. Cl.
CPC .............. *H01L 31/12* (2013.01); *H01L 31/14* (2013.01); *H01L 31/141* (2013.01); *H01L 31/143* (2013.01); *H01L 31/145* (2013.01); *H01L 31/153* (2013.01); *H01L 31/16* (2013.01); *H01L 31/173* (2013.01); *H01L 51/0097* (2013.01); *H01L 51/448* (2013.01); *H01L 51/5253* (2013.01); *A61B 5/02433* (2013.01); *A61B 2562/0238* (2013.01)

(56) References Cited

U.S. PATENT DOCUMENTS

| | | | |
|---|---|---|---|
| 2018/0011015 A1* | 1/2018 | Ishii | G01N 21/4795 |
| 2019/0038224 A1* | 2/2019 | Zhang | A61B 5/6824 |
| 2019/0076100 A1* | 3/2019 | Narkiss | A61B 5/746 |
| 2019/0090788 A1* | 3/2019 | Nam | A61B 5/1455 |
| 2019/0200866 A1* | 7/2019 | Eom | A61B 1/0638 |

FOREIGN PATENT DOCUMENTS

| | | |
|---|---|---|
| JP | 2016-000205 A | 1/2016 |
| JP | 10-2017-0019882 A | 2/2017 |

OTHER PUBLICATIONS

Lee et al. "Toward all-day wearable health monitoring: An ultralow-power, reflective organic pulse oximetry sensing patching" Science Advances, Nov. 9, 2018.

KR Office Action in application No. 10-2018-0037002 dated Jul. 31, 2019.

* cited by examiner

BIO-INFORMATION DETECTING SENSOR

CROSS-REFERENCE TO RELATED APPLICATION

This application claims priority to and the benefit of Korean Patent Application No. 10-2018-0037002, filed on Mar. 30, 2018, the disclosure of which is incorporated herein by reference in its entirety.

BACKGROUND

1. Field of the Invention

The present invention relates to a bio-information detecting sensor, and more particularly, to a bio-information detecting sensor capable of measuring heartbeat and oxygen saturation in blood.

2. Discussion of Related Art

Generally, in a medical institution or general household, bio-information detecting sensors for detecting heart rates, respiration, other bio-activities, and the like are used.

For example, there is a heartbeat and oxygen saturation sensor capable of measuring oxygen saturation in blood using light absorption of hemoglobin. The heartbeat and oxygen saturation sensor using optical elements can relatively simply noninvasively detect bio-information.

A conventional heartbeat and oxygen saturation sensor using an optical element can be divided into a transmission type sensor or a reflection type sensor according to a type thereof.

In the transmission type sensor, a bio-medium (such as a finger or earlobe) is placed between a light emitting diode (LED) and a photodiode (PD), and light emitted from the LED passes through the bio-medium and is received by the PD so that bio-information is obtained.

In the reflection type sensor, an LED is disposed to be coplanar with a PD, the LED emits light to a bio-medium, and the PD receives the light reflected by the bio-medium so that biomedical information is obtained.

Light passing through a bio-medium tends to be distributed more widely than an incident angle of the emitted light due to a scattering effect inside the bio-medium, and since degrees of absorption and scattering vary according to a wavelength of the emitted light, a difference in light distribution in which the light is concentrated tends to occur.

Conventional transmission and reflection type heartbeat and oxygen saturation sensors are generally formed by arranging optical elements based on silicon or III-V compound semiconductors. Such conventional inorganic semiconductor-based optical elements have difficulty in securing mechanical flexibility and stretchability, and thus are limited in application to various parts of a body. In addition, a spatial arrangement of light emitting elements and light receiving elements should be optimized to efficiently receive light, but the conventional inorganic semiconductor-based optical elements are mainly formed in a rectangular shape, and thus are very limited in design freedom for obtaining high efficiency signals. Since a wearable health care sensor capable of monitoring at all times requires small power consumption of a light source for securing a sufficient signal, the limit of design freedom of a present technology can be a serious problem in reduction of the power consumption.

SUMMARY OF THE INVENTION

The present invention is directed to providing a bio-information detecting sensor capable of effectively receiving light.

The present invention is also directed to providing a bio-information detecting sensor capable of reducing a manufacturing cost and being driven with ultra-low power.

However, objectives of the present invention are not limited to the above-described objectives and may be variously modified without departing from the spirit and scope of the present invention.

According to an aspect of the present invention, there is provided a bio-information detecting sensor including a flexible substrate, light emitting parts disposed on the flexible substrate, and a light receiving part disposed on the flexible substrate and having a donut shape surrounding the light emitting parts.

The plurality of light emitting parts may be formed, and the light receiving part may surround the plurality of light emitting parts.

The light emitting parts may include a first light emitting part and a second light emitting part. The light receiving part may include a first hole in which the first light emitting part is disposed and a second hole in which the second light emitting part is disposed.

The first light emitting part and the second light emitting part may be disposed apart from the light receiving part by a predetermined distance.

The light receiving part may have a shape of a number 8.

A wavelength of light emitted by the first light emitting part may be different from a wavelength of light emitted by the second light emitting part.

Each of the first light emitting part and the second light emitting part may include an organic light emitting diode The first light emitting part may include a green organic light emitting diode or an infrared organic light emitting diode, and the second light emitting part may include a red organic light emitting diode.

The light receiving part may include an organic photodiode.

The light receiving part may include a first light receiving part having the first hole and a second light receiving part having the second hole, and an area of an upper surface of the first light receiving part may be different from that of an upper surface of the second light receiving part.

An opening of each of the first hole and the second hole may have any one among circular, elliptical, and polygonal shapes.

The bio-information detecting sensor may further include a resin layer disposed on the flexible substrate and a cover substrate disposed on the resin layer, wherein the resin layer may cover the light emitting parts and the light receiving part, and each of the flexible substrate and the cover substrate may include a protective layer configured to prevent permeation of moisture or oxygen.

The resin layer may include an ultraviolet-curing resin layer.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Figure 1:
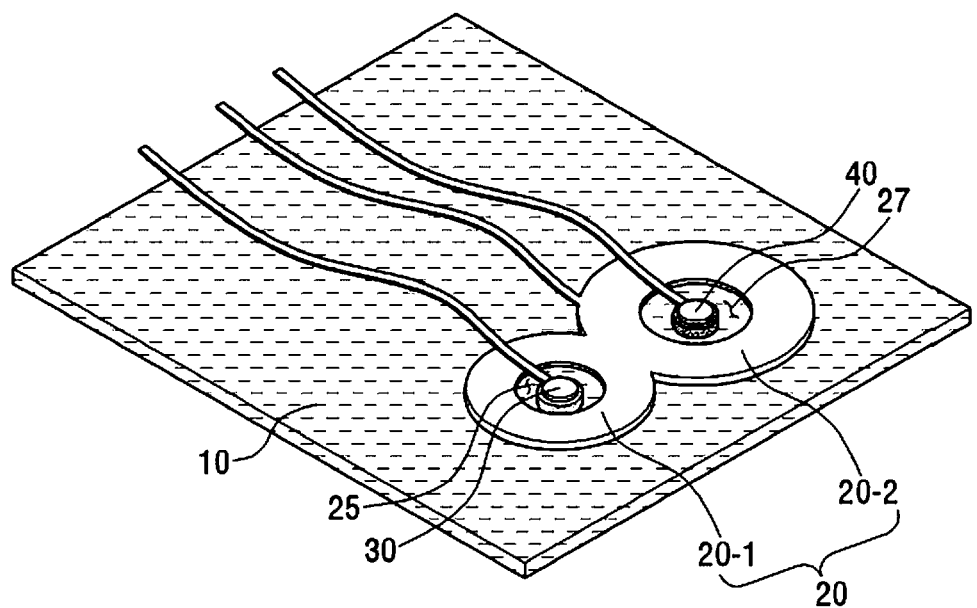
FIG. 1 is a view illustrating a bio-information detecting sensor according to an embodiment of the present invention.

The objectives, features, advantages of the present invention will be more clear with reference to the following detailed descriptions related to the accompanying drawings. Since the invention can be variously modified and have various embodiments, accordingly, specific embodiments thereof will be illustrated in the drawings and described in detail below.

In the drawings, the thicknesses of layers and regions are exaggerated for clarity, and when an element or layer is referred to as "being on" or "being above" another element or layer includes a case in which the element is directly present on the other element or layer and also includes a case in which the element is present on the other element or layer with another element or layer interposed therebetween. Like reference numerals essentially refer to like elements throughout the specification. In addition, elements having the same functions within the same spiritual range illustrated in the drawings will be described with the same reference numerals.

The detailed descriptions of known functions and configurations related to the present invention will be omitted when it is determined that the detailed descriptions may unnecessarily obscure the gist of the present invention. In addition, numerals (for example, a first, a second, and the like) used in the specification are only identifiers for distinguishing one component from the other.

In addition, suffixes such as "module" and "part" for elements used in the following description are given or mixed only in consideration of ease of specification description and do not have their own meanings or roles.

Hereinafter, embodiments of the present invention will be described in more detail with reference to the accompanying drawings. Among elements of the present invention, detailed descriptions of elements which may be clearly understood and easily reproduced by those skilled in the art will be omitted so as not to obscure the gist of the present invention.

Hereinafter, a bio-information detecting sensor according to the present invention will be described.

Figure 2:
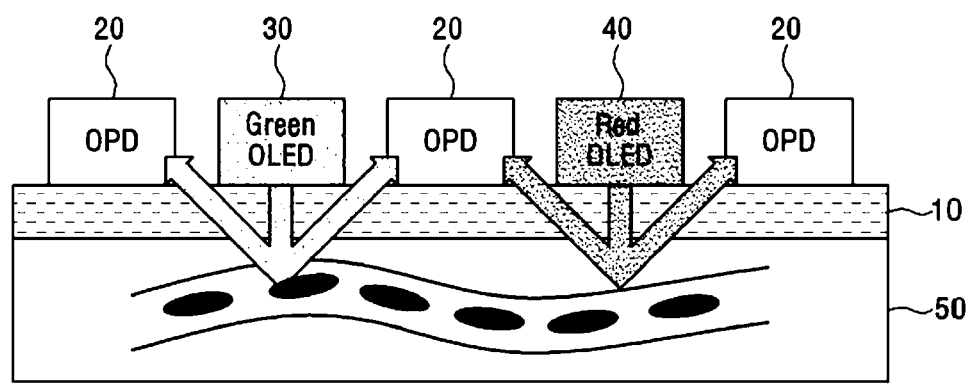
FIG. 2 is a conceptual view for describing an operation principle of the bio-information detecting sensor of FIG. 1.
Figure 3:
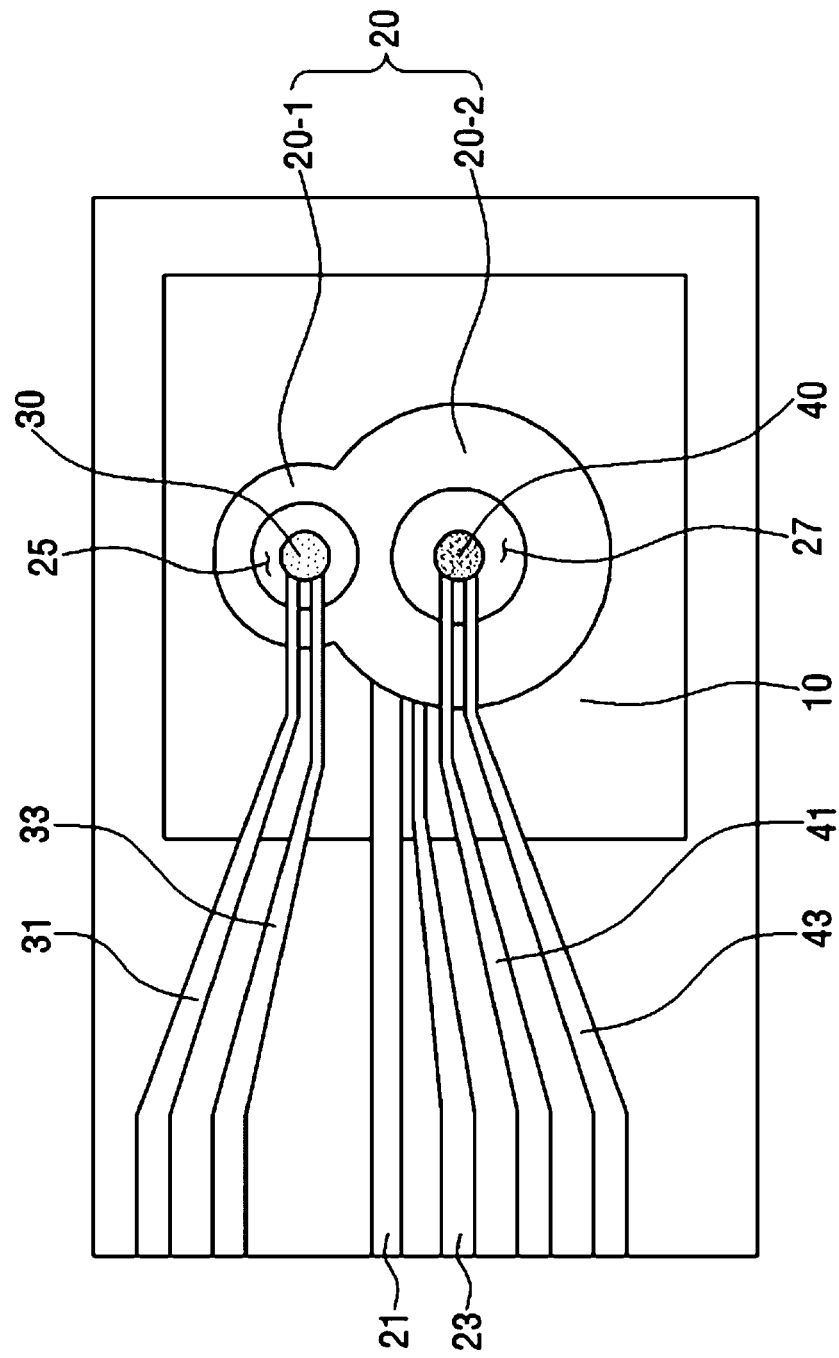
FIG. 3 is a plan view illustrating the bio-information detecting sensor of FIG. 1.

FIG. 1 is a view illustrating the bio-information detecting sensor according to an embodiment of the present invention, FIG. 2 is a conceptual view for describing an operation principle of the bio-information detecting sensor of FIG. 1, and FIG. 3 is a plan view illustrating the bio-information detecting sensor of FIG. 1.

Referring to FIGS. 1 to 3, the bio-information detecting sensor according to the embodiment of the present invention may include a flexible substrate 10, a light receiving part 20, and light emitting parts 30 and 40.

<Flexible Substrate 10>

The flexible substrate 10 has a flexible property and is attached to a surface of a body (target object) 50. Various components for sensing bio-information may be disposed on the flexible substrate 10.

The flexible substrate 10 may be a synthetic resin. Specifically, the flexible substrate 10 may be polyethylene terephthalate (PET).

Like a general substrate, a circuit pattern of electric wires for connecting various components (circuit components and the like) may be formed on the flexible substrate 10 on the basis of a circuit design, and electric conductors may be formed on an insulator.

In addition, the components such as electric parts may be mounted on the flexible substrate 10, the wires for connecting the components in a circuit may be formed on the flexible substrate 10, and components which do not have functions of electrically connecting the other components may be mechanically fixed on the flexible substrate 10.

In addition, according to the embodiment of the present invention, the flexible substrate 10 may not include the electric wires such as a circuit and components such as electric parts, but the light receiving part 20 and the light emitting parts 30 and 40 may be disposed on the flexible substrate 10.

The light receiving part 20 and the light emitting parts 30 and 40, which will be described below, may be disposed on the flexible substrate 10. In addition, various components (parts) used for detecting bio-information may be mounted on the flexible substrate 10.

Since the substrate is attached to the body (target object) 50 and detects the bio-information, the substrate should be capable of being in close contact with the body 50 in order to detect the accurate bio-information. Therefore, the flexible substrate 10 according to the embodiment of the present invention may be partially bent to have a curved surface so as to be in close contact with the body 50 partially having a curved surface. That is, the flexible substrate 10 may be bent to partially have a flat surface and a curved surface.

The flexible substrate 10 may include a protective layer which prevents permeation of air containing moisture and/or oxygen. The flexible substrate 10 attached to the body 50 may prevent air containing moisture and oxygen contained in the body from permeating the bio-information detection sensor of the present invention. The flexible substrate 10 may prevent various foreign substances in addition to moisture and air, which degrade accuracy of the bio-information detecting sensor of the present invention, from being introduced into the sensor.

<Light Receiving Unit 20>

In the bio-information detecting sensor according to the embodiment of the present invention illustrated in FIGS. 1 to 3, the plurality of light emitting parts 30 and 40, which will be described below, include a first light emitting part 30 and a second light emitting part 40.

The light receiving part 20 of the bio-information detecting sensor according to the embodiment of the present invention may be disposed on the flexible substrate 10 and may have a donut shape surrounding the light emitting parts 30 and 40.

The bio-information detecting sensor according to the embodiment of the present invention may have one light emitting part 30 or 40 of FIG. 1 or the plurality of light emitting parts 30 and 40. The light receiving part 20 may have a donut shape surrounding one light emitting part 30 or 40 of FIG. 1 when there is one light emitting part 30 or 40 of FIG. 1. When there are the plurality of light emitting parts 30 and 40, the light receiving part 20 may have the donut shape surrounding the plurality of light emitting parts 30 and 40. Specifically, when there are two light emitting parts 30 and 40, the light receiving part 20 may have a shape of a number 8.

The donut shape in the present invention includes a general circular donut shape and also includes various donut shapes having a polygonal shape in addition to the circular shape.

The light receiving part 20 may include a first hole 25 and a second hole 27. The first light emitting part 30 may be disposed in the first hole 25, and the second light emitting part 40 may be disposed in the second hole 27.

The light receiving part 20 of the bio-information detecting sensor according to the embodiment of the present invention may receive an optical signal, which is emitted to the body 50, of each of the light emitting parts 30 and 40 and generate a photocurrent signal.

Various components (parts) capable of receiving the optical signal may be used in the light receiving part 20.

Specifically, the light receiving part 20 may be a photodiode (PD), a photomultiplier, a phototransistor, or an organic photodiode (OPD).

In general, a PD is an example of a photoelectric conversion element or a photodetector capable of converting optical energy into a current or voltage. The PD has a P-N junction or P-intrinsic region-N (PIN) structure. The PD generates free electrons and holes using a photoelectric effect.

More specifically, the PD is a kind of an optical sensor which converts optical energy into electrical energy to obtain an electric signal (current or voltage) from an optical signal and is a semiconductor device which is provided with a photodetection function at a junction of a diode. Such a PD basically utilizes a principle that photons are absorbed to generate electrons or holes to change a conductivity of a diode according to an optical signal. That is, a current of the PD essentially changes according to a generation rate of an optically generated carrier, and an optical signal which is changed according to time is converted into an electric signal due to this characteristic.

The PD is used in various fields such as an optical communication field using the above-described characteristic like an optical sensor.

The light receiving part 20 may be disposed on the flexible substrate 10. Specifically, the light receiving part 20 may be disposed or formed on one surface of the flexible substrate 10, and a surface of the body (target object) 50 may be disposed on the other surface (surface opposite to one surface) of the flexible substrate 10.

The light receiving part 20 receives power from an apparatus including the bio-information detecting sensor according to the embodiment of the present invention through power supply lines 21 and 23 and receives optical signals, which are emitted to the body 50, of the first light emitting part 30 and the second light emitting part 40. Bio-information such as heartbeat and oxygen saturation of the body 50 may be obtained from the received optical signals.

The light receiving part 20 may include the first hole 25 and the second hole 27. Openings of the first hole 25 and the second hole 27 may have shapes corresponding to shapes, when viewed from above, of the first light emitting part 30 and the second light emitting part 40 disposed in the first hole 25 and the second hole 27.

Specifically, when each of the first light emitting part 30 and the second light emitting part 40 viewed from above has a circular, elliptical, or polygonal shape, the opening of each of the first hole 25 and the second hole 27 may have any one of a corresponding circular, elliptical, or polygon shape. The shapes of the openings of the first hole 25 and the second hole 27 are not limited to the shapes corresponding to the shapes of the first light emitting part 30 and the second light emitting part 40 viewed from above, the openings of the first hole 25 and the second hole 27 may have shapes different from those of the first light emitting part 30 and the second light emitting part 40 viewed from above as long as light reflected by the body 50 may be effectively received.

The light receiving part 20 may include a first light receiving part 20-1 having the first hole 25 and a second light receiving part 20-2 having the second hole 27.

The first hole 25 may be formed in the first light receiving part 20-1 and the second hole 27 may be formed in the second light receiving part 20-2.

The first light receiving part 20-1 may receive an optical signal emitted to the body 50 by the first light emitting part 30 disposed in the first hole 25. Since the first light receiving part 20-1 entirely surrounds a side surface of the first light emitting part 30, the optical signal generated by the first light emitting part 30 may be reflected by the body 50 to reach the first light receiving part 20-1 in all directions.

The second light receiving part 20-2 may receive an optical signal emitted to the body 50 by the second light emitting part 40 disposed in the second hole 27. Since the second light receiving part 20-2 entirely surrounds a side surface of the second light emitting part 40, the optical signal generated by the second light emitting part 40 may be reflected by the body 50 to reach the second light receiving part 20-2 in all directions.

An area of an upper surface of the first light receiving part 20-1 in which the first hole 25 is formed and an area of an upper surface of the second light receiving part 20-2 in which the second hole 27 is formed may be different. Specifically, the area of the upper surface of the second light receiving part 20-2 may be greater than that of the upper surface of the first light receiving part 20-1.

The areas of the upper surface of the first light receiving part 20-1 and the second light receiving part 20-2 may be determined according to wavelengths of light emitted to the body 50 by the first light emitting part 30 disposed in the first hole 25 and the light emitting part 40 disposed in the second hole 27, a scattering mechanism of light reflected by the body 50, and the like.

The areas of the upper surfaces of the first light receiving part 20-1 and the second light receiving part 20-2 may be determined such that amounts of optical signals, which are generated by the first light emitting part 30 and the second light emitting part 40 and reflected by the body 50 to reach the first light receiving part 20-1 and the second light receiving part 20-2, are maximized.

<Light Emitting Parts 30 and 40>

The bio-information detecting sensor according to the embodiment of the present invention may include the light emitting parts 30 and 40. The light emitting parts 30 and 40 may be disposed on the flexible substrate and may be surrounded by the donut-shaped light receiving part 20.

Each of the light emitting parts 30 and 40 may emit (radiate) light. Various components (parts) capable of emitting light may be used as the light emitting parts 30 and 40. Specifically, each of the light emitting parts 30 and 40 may be a light emitting diode (LED), an infrared LED, a laser diode, or an organic LED.

One light emitting part 30 or 40 or the plurality of light emitting parts 30 and 40 may be formed in the bio-information detecting sensor according to the embodiment of the present invention. The light emitting parts 30 and 40 may include the first light emitting part 30 and the second light emitting part 40 when there are the plurality of light emitting parts 30 and 40. A wavelength of light emitted by the first light emitting part 30 may be different from a wavelength of light emitted by the second light emitting part 40.

Hereinafter, the first light emitting part 30 and the second light emitting part 40 will be described.

The first light emitting part 30 of the bio-information detecting sensor according to the embodiment of the present invention may be an OLED.

Specifically, the first light emitting part 30 may be a green OLED or an infrared OLED.

A general OLED is a thin film LED including an organic compound film in which a light emission layer emits light in response to an electric current. Specifically, the general OLED includes organic compound layers formed between an anode electrode and a cathode electrode. The organic compound layers include a hole injection layer (HIL), a hole transport layer (HTL), an emission layer (EML), an electron transport layer (ETL), and an electron injection layer (EIL).

When a driving voltage is applied to the anode electrode and the cathode electrode, holes passing through the HTL and electrons passing through the ETL move to the EML to generate excitons so that visible light is generated in the EML.

The green OLED includes an EML containing a green light emitting material, and the green light emitting material is known in the art. In addition, the infrared OLED includes an EML containing an infrared light emitting material, and the infrared light emitting material is known in the art.

The first light emitting part 30 may be disposed in the first hole 25 of the light receiving part 20. The first light emitting part 30 may be disposed in the first hole 25 to be spaced apart from the light receiving part 20 by a predetermined distance.

The first light emitting part 30 may be disposed in the first hole 25 of the light receiving part 20 and the flexible substrate 10. The first light emitting part 30 disposed in the first hole 25 may be spaced apart from the light receiving part 20 by the predetermined distance, and when the opening of the first hole 25 has a circular shape, since the first light emitting part 30 is disposed at a center of the first hole 25, the predetermined distance may be constant.

The first light emitting part 30 may be disposed at the center of the first hole 25 regardless of the shape of the opening of the first hole 25 of the light receiving part 20. However, the first light emitting part 30 may not be disposed at the center of the first hole 25 such that the light receiving part 20 effectively receives light, which is emitted to the body 50, of the first light emitting part 30.

The first light emitting part 30 may emit an optical signal to the body 50. The first light emitting part 30 may be attached to the flexible substrate 10 and emit the optical signal toward the body 50.

The first light emitting part 30 may receive power from the apparatus including the bio-information detecting sensor according to the embodiment of the present invention through power supply lines 31 and 33 and emit received energy as light with a specific wavelength.

When the first light emitting part 30 is a green OLED, the first light emitting part 30 emits green light, and when the first light emitting part 30 is an infrared OLED, the first light emitting part 30 emits infrared light.

The first light emitting part 30 viewed from above may have a circular shape but is not limited thereto and may have an elliptical or polygonal shape. The shape of the first light emitting part 30 viewed from above is not particularly determined, and the first light emitting part 30 which has any shape may be used in the bio-information detecting sensor of the present invention.

The second light emitting part 40 of the bio-information detecting sensor according to the embodiment of the present invention may be an OLED.

Specifically, the second light emitting part 40 may be a red OLED.

The red OLED includes an EML containing a red light emitting material, and the red light emitting material is well known in the art.

The second light emitting part 40 may be disposed in the second hole 27 of the light receiving part 20. The second light emitting part 40 may be disposed in the second hole 27 to be spaced apart from the light receiving part 20 by a predetermined distance.

The second light emitting part 40 may be disposed in the second hole 27 of the light receiving part 20 and the flexible substrate 10. The second light emitting part 40 disposed in the second hole 27 may be disposed apart from the light receiving part 20 by a predetermined distance, and when the opening of the second hole 27 has the circular shape, since the second light emitting part 40 is disposed at a center of the second hole 27, the predetermined distance may be constant.

The second light emitting part 40 may be disposed at the center of the second hole 27 regardless of the shape of the opening of the second hole 27 of the light receiving part 20. However, the second light emitting part 40 may not be disposed at the center of the second hole 27 such that the light receiving part 20 effectively receives light, which is emitted to the body 50, of the second light emitting part 40.

The second light emitting part 40 may emit an optical signal to the body 50. The second light emitting part 40 may be attached to the flexible substrate 10 and may emit the optical signal toward the body 50.

The second light emitting part 40 may receive power from the apparatus including the bio-information detecting sensor according to the embodiment of the present invention through power supply lines 41 and 43 and emit received energy as light with a specific wavelength.

When the second light emitting part 40 is a red OLED, the second light emitting part 40 emits red light.

The second light emitting part 40 viewed from above may have a circular shape but is not limited thereto and may have an elliptical or polygonal shape. The shape of the second light emitting part 40 viewed from above is not particularly determined, and the second light emitting part 40 having any shape may be used in the bio-information detecting sensor of the present invention.

The light receiving part 20 and the light emitting parts 30 and 40 may be covered with a resin layer 60 to protect the light receiving part 20 and the light emitting parts 30 and 40 according to the embodiment of the present invention. Hereinafter, the resin layer will be described.

The bio-information detecting sensor according to the embodiment of the present invention may efficiently utilize light emitted from the OLED because a refractive index is matched between the body (target object) 50 such as skin and the substrate to emit the light trapped in the substrate.

Specifically, in the case of the OLED formed on the flexible substrate 10, there is an effect in that light trapped in the substrate 10 is emitted to the body 50 due to the refractive index matching between the flexible substrate 10 and the body 50. In other words, due to characteristics of the thin film OLED formed on the flexible substrate 10, the bio-information detecting sensor of the present invention may be in close contact with the body 50, and due to the refractive index matching between the substrate 10 in which the OLED is formed (or disposed) and the body 50, more light may be transmitted to the body 50.

Figure 4:
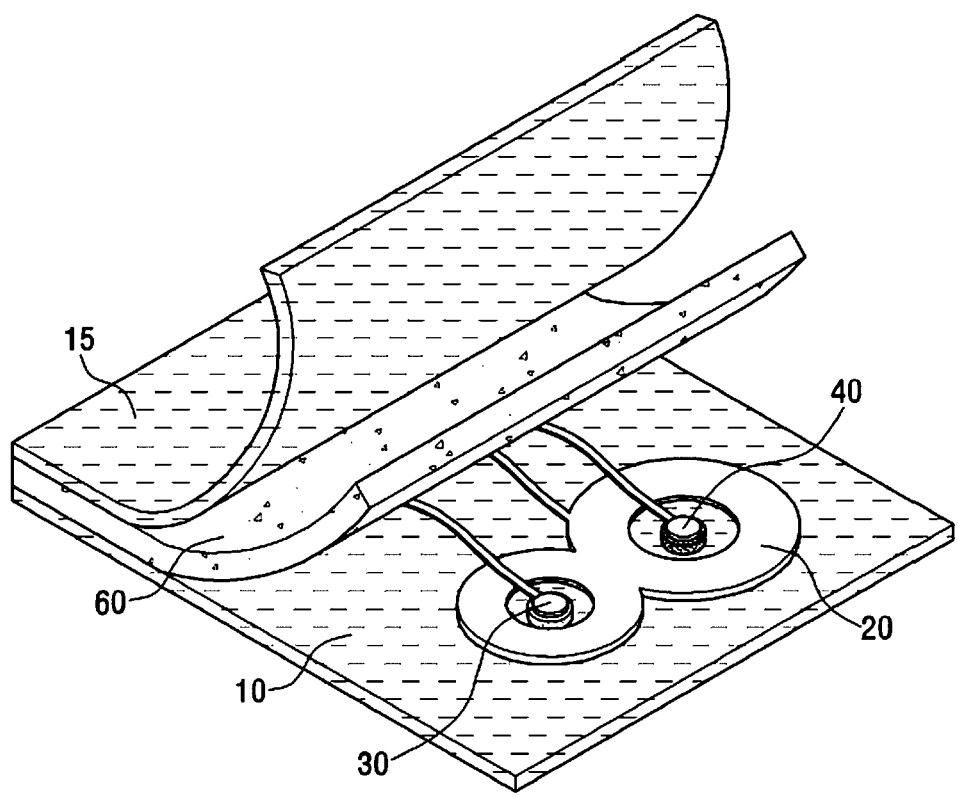
FIG. 4 is a view illustrating a case in which a resin layer is included in the bio-information detecting sensor of FIG. 1.

FIG. 4 is a view illustrating a case in which the resin layer is included in the bio-information detecting sensor of FIG. 1.

Referring to FIG. 4, the bio-information detecting sensor according to the embodiment of the present invention may further include the resin layer 60 disposed on the flexible substrate.

The resin layer 60 may cover the light receiving part 20 and the light emitting parts 30 and 40. According to the embodiment of the present invention, the resin layer 60 may be an ultraviolet-curing resin layer 60.

The resin layer 60 may protect the light receiving part 20 and the light emitting parts 30 and 40 from moisture and/or oxygen to a certain extent and prevent various components (parts) including the light receiving part 20 and the light emitting parts 30 and 40 mounted on the flexible substrate 10 from being detached from the flexible substrate 10.

When a cover substrate 15, which will be described below, is disposed on the resin layer 60 according to the embodiment of the present invention, the flexible substrate 10 and the cover substrate 15 are bonded with the resin layer 60.

<Cover Substrate 15>

The bio-information sensing sensor according to the embodiment of the present invention may further include the cover substrate 15. The cover substrate 15 may be disposed on the resin layer.

According to the embodiment of the present invention, the cover substrate 15 may be formed of the same material as that of the flexible substrate 10. The cover substrate 15 may be formed of a synthetic resin which is the same as that of the flexible substrate 10. Specifically, the cover substrate 15 may be formed of polyethylene terephthalate (PET). However, according to the embodiment of the present invention, the cover substrate 15 is not limited to being formed of the same material as that of the flexible substrate 10 but may be formed of other materials.

The cover substrate 15 may have a flexible property (bending property) which is the same as that of the flexible substrate 10. In addition, since the cover substrate 15 is not in directly contact with the body 50, the cover substrate 15 may not have a flexible property (bending property). One surface of the cover substrate 15 in contact with the resin layer 60 may have the flexible property (bending property) and the other surface exposed to the outside may not have a flexible property (bending property) in order to protect the components of the bio-information detecting sensor of the present invention.

According to a circuit design, electric wires for connecting various components (circuit components and the like) may be formed as a circuit pattern on the cover substrate 15 like a general substrate, and an electric conductor may be formed on an insulator.

In addition, components such as electric parts may be mounted on the cover substrate 15, wires for connecting the components in a circuit may be formed on the cover substrate 15, and components which do not have functions of electrically connecting the other components may be mechanically fixed.

In addition, according to the embodiment of the present invention, the cover substrate 15 may not include the electric wires such as a circuit and components such as electric parts.

The cover substrate 15 may include a protective layer which prevents permeation of air containing moisture and/or oxygen. The cover substrate 15 may prevent air containing moisture and oxygen of a human body and the air from being introduced into the bio-information detecting sensor of the present invention.

The cover substrate 15 may prevent various foreign substances in addition to the moisture and the air, which degrade accuracy of the bio-information detecting sensor of the present invention, from being introduced into the sensor.

A method of manufacturing the bio-information detecting sensor according to the embodiment of the present invention will be briefly described below.

Figure 5:
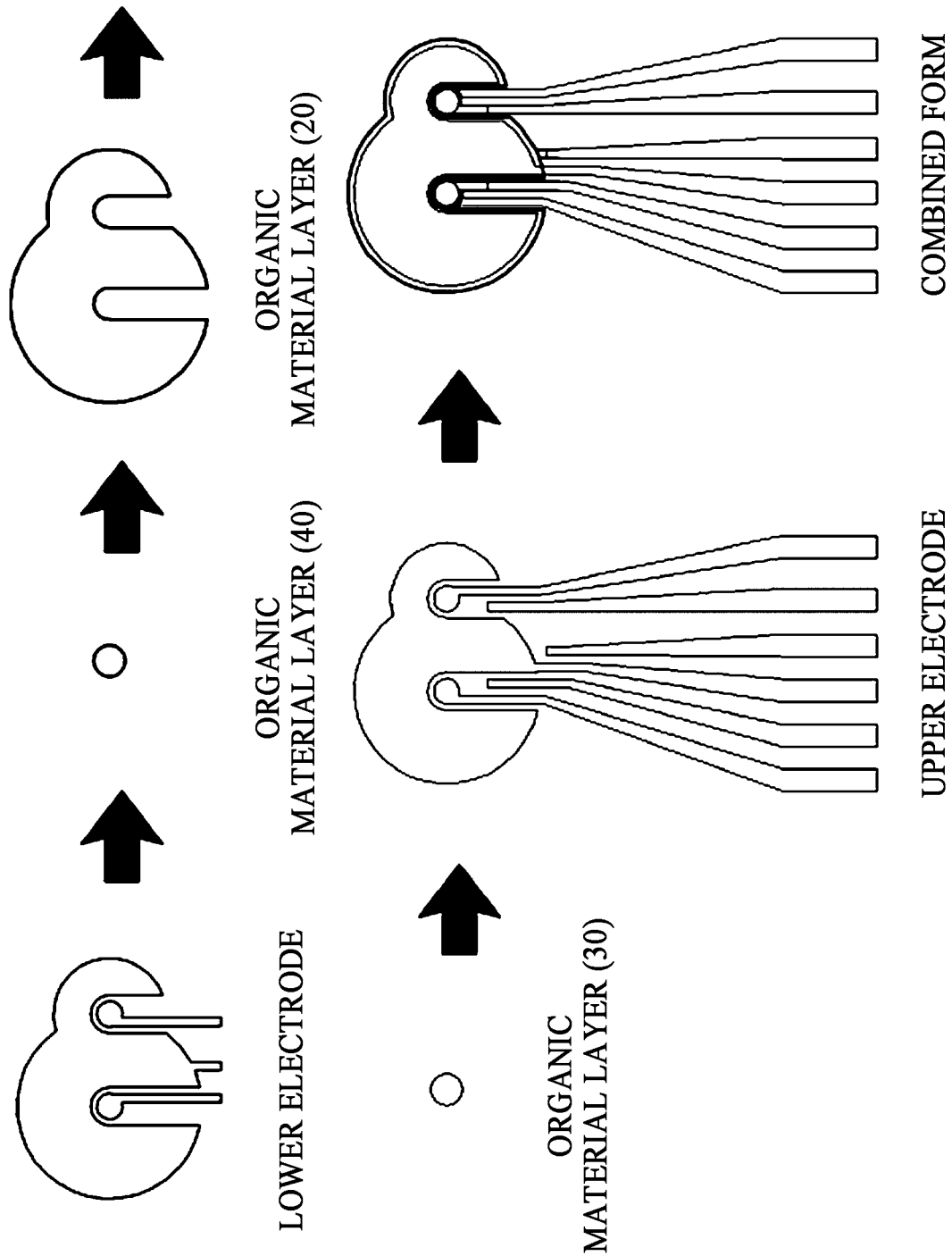
FIG. 5 is a conceptual view illustrating a method of manufacturing the bio-information detecting sensor according to the embodiment of the present invention.

FIG. 5 is a conceptual view illustrating a method of manufacturing the bio-information detecting sensor according to the embodiment of the present invention.

In the method of manufacturing the bio-information detecting sensor according to the embodiment of the present invention illustrated in FIG. 5, the plurality of light emitting parts 30 and 40 include the first light emitting part 30 and the second light emitting part 40, and the OPD is used as the light receiving part 20 and the OLED is used as each of the first light emitting part 30 and the second light emitting part 40.

Referring to FIG. 5, lower electrodes may be formed on the flexible substrate 10. The lower electrodes may be wires for supplying power to the light receiving part 20, the first light emitting part 30, and the second light emitting part 40.

After the lower electrodes are formed, an organic material layer may be disposed to form each of the light receiving part 20, the first light emitting part 30, and the second light emitting part 40. In FIG. 5, the second light emitting part 40, the light receiving part 20, and the first light emitting part 30 are sequentially illustrated, but the present invention is not limited to the illustrated order, and the organic material layer for forming each of the light receiving part 20, the first light emitting part 30, and the second light emitting part 40 may be disposed regardless of the order.

After the light receiving part 20, the first light emitting part 30, and the second light emitting part 40 are formed, upper electrodes may be formed. The upper electrodes may be wires for supplying power to the light receiving part 20, the first light emitting part 30, and the second light emitting part 40.

In the bio-information detecting sensor according to the embodiment of the present invention, when the lower electrode is a positive (+) electrode, the upper electrode is a negative (−) electrode, and when the lower electrode is a negative (−) electrode, the upper electrode is a positive (+) electrode.

In the embodiment of the present invention, the lower electrodes are positive (+) electrodes, and the upper electrodes are negative (−) electrodes.

The light receiving part 20, the first light emitting part 30, the second light emitting part 40, the lower electrodes, the upper electrodes, and the flexible substrate 10 may be covered with the resin layer 60 after the upper electrodes are formed.

The resin layer 60 may be formed to have a predetermined size and a predetermined thickness to cover the bio-information detecting sensor according to the embodiment of the present invention by a spin coating method. After the light receiving part 20, the first light emitting part 30, the second light emitting part 40, the lower electrodes, and the upper electrodes are disposed on the flexible substrate 10, the light receiving part 20, the first light emitting part 30, the second light emitting part 40, the lower electrodes, and the upper electrodes may be covered with the resin layer 60.

According to the embodiment of the present invention, only some of the light receiving part 20, the first light emitting part 30, the second light emitting part 40, the lower electrodes, the upper electrodes, and the flexible substrate 10 may be covered with the resin layer 60. According to the embodiment of the present invention, only some of the components, which are particularly required to be protected, may be covered with the resin layer 60.

Figure 6:
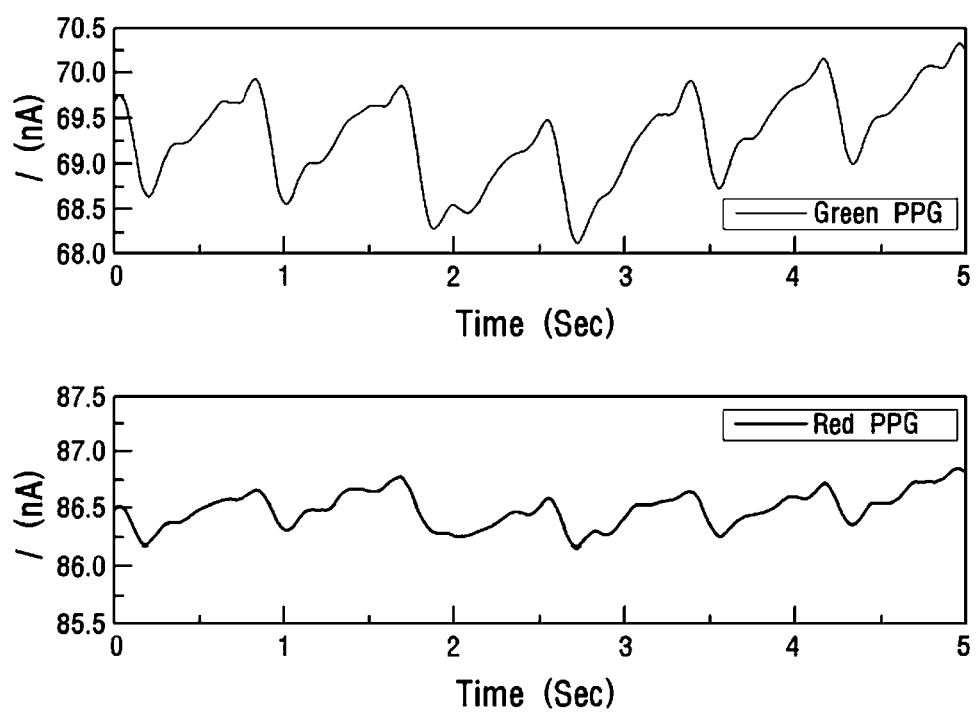
FIG. 6 is a view showing an output (photoplethysmography (PPG)) signal of a commercial sensor.
Figure 7:
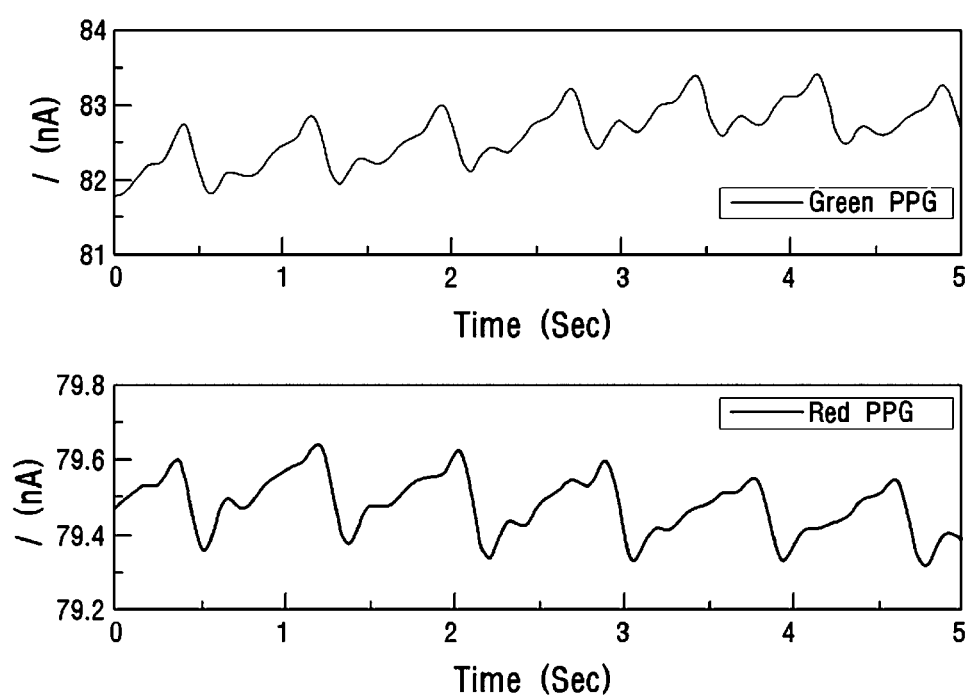
FIG. 7 is a graph showing a PPG signal of the bio-information detection sensor of FIG. 1.

FIG. 6 is a view showing an output (photoplethysmography (PPG)) signal of a commercial sensor, and FIG. 7 is a graph showing a PPG signal of the bio-information detection sensor of FIG. 1.

Referring to FIGS. 6 and 7, FIG. 6 shows the PPG signal obtained by the currently used commercial sensor, and FIG. 7 shows the PPG signal obtained by the bio-information detecting sensor according to the embodiment of the present invention. The commercial sensor is a reflective sensor to which a green LED and a red LED are applied, and a PPG signal represents a heartbeat signal or photoplethysmogram.

In the bio-information detecting sensor according to the embodiment of the present invention illustrated in FIG. 7, the plurality of light emitting parts 30 and 40 include the first light emitting part 30 and the second light emitting part 40, the OPD is used as the first light receiving part 20, and the OLED is used as each of the first light emitting part 30 and the second light emitting part 40. Specifically, the green OLED is used as the first light emitting part 30, and the red OLED is used as the second light emitting part 40.

Light of each of the light emitting parts 30 and 40 disposed on the flexible substrate 10 is emitted to the body 50 through the flexible substrate 10, and an intensity of the light reflected by movement of blood may be sent to the light receiving part 20 disposed on the flexible substrate 10. A change in the intensity of the light received by the light receiving part 20 according to time due to movement of a blood vessel changes a current output from the light receiving part 20.

PPG signals may be obtained from the first light emitting part 30 and the second light emitting part 40 through the bio-information detecting sensor according to the embodiment of the present invention, and bio-information such as heartbeat and oxygen saturation may be obtained using the PPG signals.

Comparing the PPG signals of FIGS. 6 and 7, it can be seen that the bio-information detecting sensor according to the embodiment of the present invention generates the PPG signals having values similar to those of PPG signals of the commercial sensor. According to FIGS. 6 and 7, the PPG signals may be obtained using the bio-information detecting sensor according to the embodiment of the present invention, and bio-information such as heartbeat and oxygen saturation may be obtained using the PPG signals.

In addition, the bio-information detecting sensor according to the embodiment of the present invention may reduce power consumption compared to the conventional commercial sensor. Table 1 below shows power consumption of each of the bio-information detecting sensor according to an embodiment of the present invention and the commercial sensor.

TABLE 1

|  | Commercial Sensor | Bio-information Detecting Sensor |
|---|---|---|
| Green Light Source Power Consumption (mW) | 0.96 | 0.31 |
| Red Light Source Power Consumption (mW) | 0.18 | 0.017 |

Referring to Table 1, in the bio-information detecting sensor according to the embodiment of the present invention, the plurality of light emitting parts 30 and 40 include the first light emitting part 30 and the second light emitting part 40, and the OLED is used as each of the first light emitting part 30 and the second light emitting part 40. Specifically, the green OLED (OLED) is used as the first light emitting part 30, and the red OLED (OLED) is used as the second light emitting part 40.

The commercial sensor shown in Table 1 is an oxygen saturation sensor (SFH7050, OSRAM) to which a green LED and a red LED are applied.

The data shown in Table 1 compares power consumptions at a point at which output PPG signals (currents received by PDs) of the bio-information detecting sensor according to the present invention and the commercial sensor are similar. In other words, the power consumptions of light emitting devices are compared at the point at which an output current of the PD of the commercial sensor is similar to an output current of the OPD of the bio-information detecting sensor of the present invention.

It can be seen that the bio-information detecting sensor according to the embodiment of the present invention consumes power which is lowered by 32.3% in the case of a green light source and lowered by 9.4% in the case of a red light source in comparison with the commercial sensor. This means that when the bio-information detecting sensor is embedded and used in a watch, a smart phone, and the like, the bio-information detecting sensor can be driven with low power for a long time by being charged once.

The bio-information detecting sensor according to the embodiment of the present invention formed based on the flexible substrate 10, the light receiving part 20, and the light emitting parts 30 and 40 is a reflective patch type sensor capable of being driven with ultra-low power.

The bio-information detecting sensor according to the embodiment of the present invention is capable of efficiently receiving light due to an arrangement structure and the shapes of the flexible substrate 10, the light receiving part 20, and the light emitting parts 30 and 40. In addition, since the light receiving part 20 and the light emitting parts 30 and 40 are used, the bio-information detecting sensor may be formed to have a shape capable of being in close contact with the body. In addition, there are advantages in that a manufacturing cost of the bio-information detecting sensor according to the embodiment of the present invention can be reduced and the bio-information detecting sensor can be driven with ultra-low power.

The bio-information detecting sensor according to the embodiment of the present invention may be applied to a conventional clip-type heartbeat and oxygen saturation sensor for medical use.

In this case, the bio-information detecting sensor according to the embodiment of the present invention may be disposed on only one surface of a clip in contact with the body 50.

In addition, the bio-information detecting sensor according to the embodiment of the present invention may be applied to a wearable device. Since the bio-information detecting sensor according to the embodiment of the present invention may be manufactured in a small size and may be driven with ultra-low power, the bio-information detecting sensor is applied to various wearable devices such as a watch, a smartphone, an earphone, underwear, glasses, and a bracelet.

In addition, the bio-information detecting sensor according to the embodiment of the present invention may be used for monitoring and detecting bio-information of an elderly or severe patient requiring continuous observation through monitoring of the body 50. The bio-information detecting sensor may be applied to a disposable patch type health care sensor using a point that the bio-information detecting sensor may be excellently driven with very low power.

A bio-information detecting sensor according to the embodiment of the present invention can effectively receive light.

In addition, the bio-information detecting sensor can be driven with very low power.

In addition, since the bio-information detecting sensor can be closely attached to a body along a shape of the body, the bio-information detecting sensor can easily and stably measure a bio-signal and can be used for various body parts.

However, effects of the present invention are not limited to the above effects but may be variously modified without departing from the spirit and scope of the present invention.

The features, structures, effects, and the like described in the above embodiments are included in at least one embodiment of the present invention, but the present invention is not necessarily limited to only one embodiment.

Furthermore, the features, structures, effects, and the like illustrated in the embodiments may be combined and modified in other embodiments by those skilled in the art. Therefore, it should be interpreted that contents related to the combinations and modifications are included in the present invention.

In addition, while the present invention has been mainly described above with reference to the embodiments, it will be understood by those skilled in the art that the invention is not limited to the embodiments, but the embodiments are only examples, and various modifications and applications which are not illustrated above may fall within the range of the present invention without departing from the essential features of the present embodiments. That is, components specifically described in the embodiments may be modified and implemented. In addition, it should be understood that differences related to modifications and applications fall within the scope of the present invention defined by the appended claims.

What is claimed is:

1. A bio-information detecting sensor comprising:
a flexible substrate;
light emitting parts disposed on the flexible substrate; and
a light receiving part disposed on the flexible substrate and having a donut shape surrounding the light emitting parts,
wherein:
the light emitting parts include a first light emitting part and a second light emitting part; and
the light receiving part includes a first hole in which the first light emitting part is disposed and a second hole in which the second light emitting part is disposed.

2. The bio-information detecting sensor of claim 1, wherein the first light emitting part and the second light emitting part are disposed apart from the light receiving part by a predetermined distance.

3. The bio-information detecting sensor of claim 1, wherein the light receiving part has a shape of a number 8.

4. The bio-information detecting sensor of claim 1, wherein a wavelength of light emitted by the first light emitting part is different from a wavelength of light emitted by the second light emitting part.

5. The bio-information detecting sensor of claim 1, wherein each of the first light emitting part and the second light emitting part includes an organic light emitting diode.

6. The bio-information detecting sensor of claim 5, wherein:
the first light emitting part includes a green organic light emitting diode or an infrared organic light emitting diode; and
the second light emitting part includes a red organic light emitting diode.

7. The bio-information detecting sensor of claim 1, wherein the light receiving part includes an organic photodiode.

8. The bio-information detecting sensor of claim 1, wherein:
the light receiving part includes a first light receiving part having the first hole and a second light receiving part having the second hole; and
an area of an upper surface of the first light receiving part is different from that of an upper surface of the second light receiving part.

9. The bio-information detecting sensor of claim 1, wherein an opening of each of the first hole and the second hole has any one among circular, elliptical, and polygonal shapes.

10. A bio-information detecting sensor comprising:
a flexible substrate;
light emitting parts disposed on the flexible substrate;
a light receiving part disposed on the flexible substrate and having a donut shape surrounding the light emitting parts;
a resin layer disposed on the flexible substrate; and
a cover substrate disposed on the resin layer,
wherein the resin layer covers the light emitting parts and the light receiving part, and each of the flexible substrate and the cover substrate includes a protective layer configured to prevent permeation of moisture or oxygen.

11. The bio-information detecting sensor of claim 10, wherein the resin layer includes an ultraviolet-curing resin layer.

* * * * *